US006641836B2

United States Patent
Hayek et al.

(10) Patent No.: US 6,641,836 B2
(45) Date of Patent: Nov. 4, 2003

(54) PROCESS FOR ENHANCING IMMUNE RESPONSE IN CANINES USING A DIETARY COMPOSITION INCLUDING GARLIC

(75) Inventors: Michael G. Hayek, Dayton, OH (US); Stefan Patrick Massimino, Dayton, OH (US); Katherine P. Boebel, West Alexandria, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/845,942

(22) Filed: Apr. 30, 2001

(65) Prior Publication Data

US 2002/0015745 A1 Feb. 7, 2002

Related U.S. Application Data

(60) Provisional application No. 60/201,028, filed on May 1, 2000.

(51) Int. Cl.$^7$ ................................................ A61K 47/00
(52) U.S. Cl. ........................ 424/439; 424/400; 424/441; 424/442; 424/484; 424/489; 426/74
(58) Field of Search .................. 424/400, 439, 424/441, 442, 484, 489; 426/74

(56) References Cited

U.S. PATENT DOCUMENTS

| | | | |
|---|---|---|---|
| 4,702,914 A | * 10/1987 | Ryan | 424/754 |
| 5,141,755 A | 8/1992 | Weisman | |
| 5,776,524 A | 7/1998 | Reinhart | |
| 5,976,549 A | 11/1999 | Lewandowski | |
| 6,007,860 A | 12/1999 | Erasmus et al. | |
| 6,156,355 A | * 12/2000 | Shields et al. | 426/61 |

FOREIGN PATENT DOCUMENTS

| | | |
|---|---|---|
| FR | 2 595 548 A | 9/1987 |
| GB | 2 321 583 A | 8/1998 |
| JP | 57192318 | 11/1982 |
| WO | WO 93 06749 A | 4/1993 |
| WO | WO 99 48381 A | 9/1999 |
| WO | WO 00 01399 A | 1/2000 |

OTHER PUBLICATIONS

L.W.V. Deboer et al: "Partial protection from platelet thrombi in canine coronaries" Federation Proceedings, vol. 46, No. 4, 1987, p. 1316.

Pinto, James T. et al.; "Effects of garlic thioallyl derivatives on growth, gluthathione concentration, and polyamine formation of human prostate carcinoma cells in culture" Am J Clin Nutr 1997; 66:398–405.

Liu, Jinzhou et al.; "Inhibition of 7,12–dimethylbenz[a] anthracene–induced mammary tumors and DNA adducts by garlic powder" Carcinogenesis 1992; 13:1847–1851.

Lau, Benjamin H.S. et al.; "Garlic compounds modulate macrophage and T–lymphocyte functions" Mol Biother 1991; 3:103–107.

\* cited by examiner

Primary Examiner—Thurman K. Page
Assistant Examiner—Charesse Evans
(74) Attorney, Agent, or Firm—Kelly L. McDow-Dunham

(57) ABSTRACT

A composition and method for enhancing immune response and improving the overall health of canines is provided which includes feeding the canines a dietary composition containing an effective amount of garlic in an amount of from about 1 to 10 g/kg diet. The dietary composition, when fed to canines, provides antioxidant, anticancer, and immunomodulatory benefits. The canines are fed the composition containing an effective amount of garlic in a quantity and frequency appropriate for their nutritional needs resulting in an enhanced immune response by increased lymphocyte blastogenesis and improves the overall health of the animal.

3 Claims, 1 Drawing Sheet

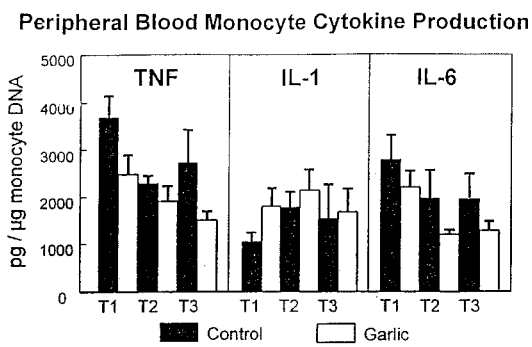

Peripheral Blood Monocyte Cytokine Production

Cytokine production by peripheral blood monocytes in response to 10 µg/mL lipopolysaccharide. There was no significant difference between the control- and garlic-fed animals for any of the cytokines measured. There was also no significant change in the garlic-fed animals compared to baseline values (T1), although there was a slight trend (not significant) for reduced TNF and IL-6 production with garlic feeding. (Mean ± SEM; n = 11, control; n = 16, garlic)

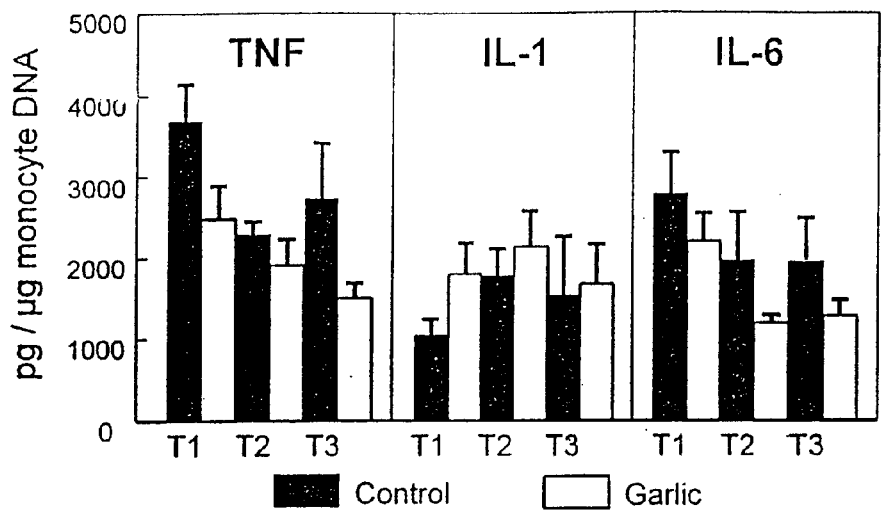

Figure 1. Cytokine production by peripheral blood monocytes in response to 10 µg/mL lipopolysaccharide. There was no significant difference between the control- and garlic-fed animals for any of the cytokines measured. There was also no significant change in the garlic-fed animals compared to baseline values (T1), although there was a slight trend (not significant) for reduced TNF and IL-6 production with garlic feeding. (Mean ± SEM; n = 11, control; n = 16, garlic)

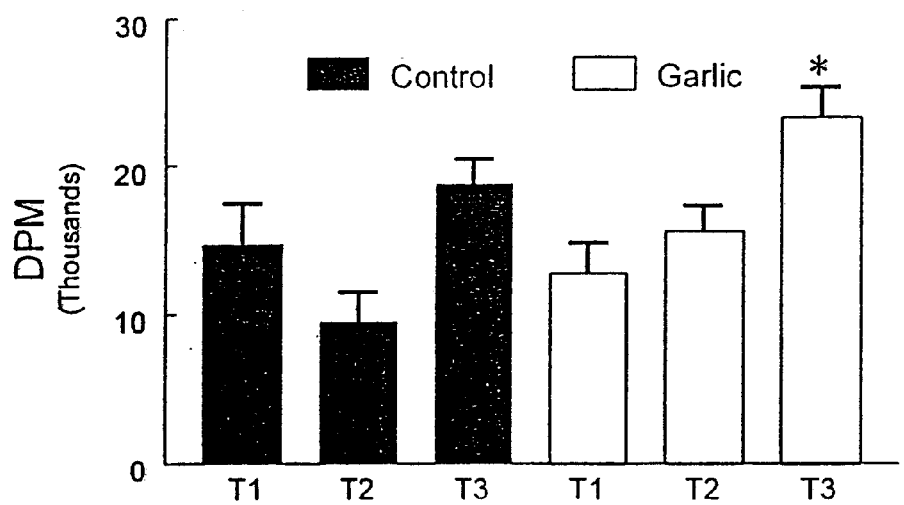

Figure 2. Lymphocyte blastogenesis in response to 10 µg/mL concanavalin A as measured by ³[H]-thymidine incorporation. There was no significant difference between the control- and garlic-fed group. However, in the garlic-fed group there was a significant increase (P<.05) in the proliferative response at T3 (*, 77 days) compared to the baseline values at T1 and a significant linear trend (P= .0003) for increased lymphocyte blastogenesis from 0 to 77 days. (Mean ± SEM; n = 11, control; n = 16, garlic)

PROCESS FOR ENHANCING IMMUNE RESPONSE IN CANINES USING A DIETARY COMPOSITION INCLUDING GARLIC

CROSS REFERENCE TO RELATED APPLICATIONS

This application claims the benefit of U.S. provisional application Ser. No. 60/201,028, filed May 1, 2000.

BACKGROUND OF THE INVENTION

This invention relates to a dietary composition and method for enhancing immune response and improving the overall health of canines, and more particularly, to a dietary composition which includes an effective amount of garlic, which, when fed to canines, provides antioxidant, anticancer, and immunomodulatory benefits.

In recent years, the health effects of garlic for humans have become an area of active research with regard to the prevention and treatment of disease. Garlic may be provided in many forms; e.g., as a natural product in raw or cooked form, as a water or oil soluble extract, a powder, and as purified forms of the bioactive compounds.

Studies have shown that organosulfur compounds found in garlic have antioxidant properties. In addition, it has been found that garlic may also function as an anticancer agent. For example, the garlic compound S-allylmercaptocysteine has been found to reduce the growth of human prostate carcinoma LNCaP cells. [1] Garlic has also been found to reduce the incidence of chemical induced tumors in rats.[2]

[1] Pinto J T, Qiao C, Xing J, Rivlin R S, Protomastro M L, Weissler M L, Tao Y, Thaler H, Heston W D, "Effects of garlic thioallyl derivatives on growth, glutathione concentration, and polyamine formation of human prostate carcinoma cells in culture" *Am J Clin Nutr* 1997; 66:398–405. [2] Liu J, Lin R I, Milner J A, "Inhibition of 7, 12-dimethylbenz[a]anthracene-induced mammary tumors and DNA adducts by garlic powder" *Carcinogenesis* 1992; 13:1847–1851.

It is also believed that the sulfur-containing components of garlic may contribute to immune modulating properties. For example, a garlic extract and a garlic protein fraction were found to increase the oxidative burst of a J744 mouse macrophage cell line and mouse peritoneal macrophages.[3]

[3] Lau B H, Yamasaki T, Gridley D S, "Garlic compounds modulate macrophage and T-lymphocyte functions" *Mol Biother* 1991; 3:103–107.

However, few studies have been conducted to evaluate the effects of garlic on companion animals such as canines. Accordingly, there is still a need in the art for a method of utilizing the health benefits of garlic in a dietary composition for canines.

SUMMARY OF THE INVENTION

The present invention meets that need by providing a process for feeding dogs a diet containing an effective amount of garlic which has been found to provide enhanced immune response and improve the overall health of the animal. Preferably, the dog is fed a diet which includes garlic in an amount of from about 1 to 10 g/kg diet.

When a composition containing an effective amount of garlic is administered to dogs in a quantity and frequency appropriate for their nutritional needs, it has been found that the immune response is enhanced by increased lymphocyte blastogenesis.

Accordingly, it is a feature of the present invention to provide a process for enhancing immune response and improving the overall health of dogs by providing an effective amount of garlic in the diet of the animal. This, and other features and advantages of the present invention, will become apparent from the following detailed description and accompanying drawings.

BRIEF DESCRIPTION OF THE DRAWINGS

FIG. 1 is a graph of cytokine production by peripheral blood monocytes in control- and garlic-fed dogs; and FIG. 2 is a graph of lymphocyte blastogenesis in control- and garlic-fed dogs.

DETAILED DESCRIPTION OF THE PREFERRED EMBODIMENTS

The present invention uses a dietary composition for dogs which contains garlic in an amount of between about 1 to 10 g/kg diet. Such a diet provides sufficient garlic to provide antioxidant, anticancer, and immunomodulatory effects.

A preferred garlic for use in the present invention is a premium garlic powder which is commercially available from Gilroy Foods. This form of garlic is preferably comprised of dehydrated garlic prepared from fresh pungent varieties of Allium sativum which has been cleaned, sliced, dehydrated and milled to powder. However, it should be appreciated that other forms of garlic which provide the desired antioxidant, anticancer, and immunomodulatory effects may also be used.

The dietary composition may be in the form of any suitable dog food formula which also provides adequate nutrition for the animal. For example, a typical canine diet for use in the present invention may contain about 20–40% crude protein, about 4–30% fat, and about 1–11% total dietary fiber on a dry matter basis. However, no specific ratios or percentages of these or other nutrients are required. The garlic may be blended with such a dietary composition to provide the beneficial amounts needed. Alternatively, the garlic may be provided in the form of a dietary supplement.

An experiment was conducted to study the potential beneficial effects of garlic on the immune response of dogs. 28 Beagle dogs (age range: 2–4 years) were fed a basal control diet for 30 days. Dogs were then randomized by body weight and divided into 2 groups. Within each group, half the dogs continued to receive the control diet and the other half were switched onto the garlic diet. This experimental period was conducted over a 77-day period. Blood was taken at the end of the baseline period (T1—day 0 of the experimental period), in the middle of the experimental period (T2—day 35) and at the end of the study (T3—day 77) in order to determine in vitro immune function (by lymphocyte blastogenesis) as well as cytokine production (tumor necrosis factor; TNF-α), interleukin-1 (IL-1), and IL-6. Urine was collected at these time points and immediately frozen in order to analyze for various markers of oxidative stress. In vivo immune function was determined by a delayed-type hypersensitivity (DTH) response test using a nonspecific antigen (phytohemagglutinin), a specific mitogen (Duramune® vaccine [Fort Dodge Laboratories]), and control (saline) to induce an inflammatory response and induration was measured at 24, 48, and 72 hours postinjection with data expressed as measurements corrected for saline. Dogs were weighed weekly and fed to maintain body weight throughout the study. Water was provided ad libitum. See Table 1 for the ingredients and composition of diets.

TABLE 1

Ingredient composition of diets

| Ingredient | g/kg | |
|---|---|---|
| | Control Diet | Garlic Diet |
| Ground corn | 510 | 510 |
| Refined poultry by-product meal | 205 | 205 |
| Poultry fat | 89 | 89 |
| Menhaden fishmeal | 85 | 85 |
| Beet pulp | 35 | 35 |
| Chicken digest | 35 | 30 |
| Dicalcium phosphate | 11 | 11 |
| Dried whole egg | 8 | 8 |
| Brewers dried yeast | 7 | 7 |
| Potassium chloride | 3 | 3 |
| Ground flax | 3 | 3 |
| Mineral mix | 3 | 3 |
| Vitamin mix | 2 | 2 |
| Sodium chloride | 2 | 2 |
| DL-methionine | 1 | 1 |
| Choline chloride | 1 | 1 |
| Garlic powder | — | 5 |

Isolation of Mononuclear Cells. Blood collected in heparinized tubes was diluted in calcium- and magnesium-free Hanks balanced salt solution (HBSS) (1:1), layered onto Ficoll-hypaque, and centrifuged at approximately 400×g for 20 minutes. The mononuclear cells were harvested, washed in HBSS, and resuspended in RPMI-1640 growth medium containing 5 mg/mL bovine serum albumin (BSA), 100 U/mL penicillin, 100 $\mu$g/mL streptomycin, and 1% L-glutamine. Cells were counted in a Coulter counter (Coulter Corporation, Hialeah, Fla.), and $1\times10^6$ cells in 7 mL of medium were plated in 60 mm well plates and allowed to adhere for 2–3 hours in a humidified $CO_2$ incubator at 37° C. The nonadherent cells were removed by gentle washing with medium, and the isolated monocytes incubated with growth medium plus 10 $\mu$g/ml of O55:B5 Eschericia coli lipopolysaccharide for 24 hours. The culture supernatant fluid was harvested, and the adherent cells digested with 1N ammonium hydroxide and 0.2% Triton X-100 for total cellular DNA quantitation.

Cytokine Assays. Bioassays for IL-1, TNF-like activity, and IL-6 were performed as previously described. Mouse plasmacytoma cell line (T1165.17), which proliferates in response to IL-1 and IL-6, was used to assay for IL-1 activity. To determine specific IL-1 activity, the IL-1 receptor on the T1165.17 cell line was blocked using a monoclonal antibody (LA 15.6) to the IL-1 receptor. Murine fibroblasts (L929) were used to assay for TNF-like activity and the IL-6 bioassay was performed using B9 cells. Data from the bioassays were expressed as pg of cytokine per $\mu$g of monocyte DNA.

Lymphocyte Blastogenesis. Mononuclear cells from the blood were isolated as described above via centrifugation on Ficoll-hypaque. After washing in HBSS cells were resuspended in culture medium containing 10% heat inactivated fetal calf serum, 100 U/mL penicillin, 100 $\mu$g/mL streptomycin, and 1% L-glutamine and adjusted to a final concentration of $1\times10^6$ cells/mL. Concanavalin A (Con A) was added to 3 wells of a 96-well plate for each sample and 200 $\mu$L of the mononuclear cell suspension added. The final concentration of Con A in each well was 10 $\mu$g/mL. The culture plates were incubated at 37° C. in a cell culture incubator for 72 hours, and then each well was pulsed with 1 $\mu$Ci of [$^3$H]thymidine (50 $\mu$L volume) and incubated an additional 24 hours. Cells were harvested on glass fiber filters (PHD cell harvester), and the amount of [$^3$H] thymidine incorporation determined (decays per minute; DPM) in a scintillation counter.

Cytokine Production. There was no significant difference between the control- and garlic-fed animals for any of the cytokines measured. There was also no significant change in the garlic-fed animals compared to baseline values (T1), although there was a slight trend (not significant) for reduced TNF and IL-6 with garlic feeding (FIG. 1).

Lymphocyte Blastogenesis. There was no significant difference between the control- and garlic-fed group in lymphocyte proliferative response to the mitogen Con A. However, in the garlic-fed group there was a significant linear trend (P=0.0003) for increased lymphocyte blastogenesis from T1 (baseline) to T3 (77 days). Moreover, lymphocyte blastogenesis was significantly increased (P<0.05) at T3 (77 days) compared to the initial baseline values at T1 (FIG. 2).

Delayed-type Hypersensitivity. There were no significant differences between the dietary groups in delayed-type hypersensitivity (DTH) response. At the midpoint of the study (35 days), there was some indication of a trend (not significant) for increased hypersensitivity to Duramune vaccine in the garlic-fed group, but this trend was not maintained and there was no evidence of a garlic effect on DTH by the end of the study.

Results

Garlic powder had no effect on cytokine production from canine peripheral blood mononuclear cells or on DTH response. However, the garlic-fed dogs had significantly enhanced lymphocyte blastogenesis compared to their baseline values.

The results demonstrate that garlic can function as an immunomodulatory agent. Garlic demonstrated an immunomodulatory effect with respect to mitogen-induced lymphocyte blastogenesis.

While certain representative embodiments and details have been shown for purposes of illustrating the invention, it will be apparent to those skilled in the art that various changes in the methods and apparatus disclosed herein may be made without departing from the scope of the invention, which is defined in the appended claims.

What is claimed is:

1. A method for increasing lymphocyte blastogenesis in a dog comprising feeding said dog a diet including an effective amount of garlic for a time sufficient for said garlic to be absorbed by said dog.

2. The method of claim 1 which said diet includes from about 1 to 10 g garlic per kg of diet.

3. The method of claim 1 wherein said diet comprising, on a dry matter basis, about 20 to 40% by weight protein, about 4 to 30% by weight fat, and about 1 to 11% dietary fiber.

* * * * *